(12) United States Patent
McGlothlin et al.

(10) Patent No.: US 8,177,740 B1
(45) Date of Patent: May 15, 2012

(54) MEDICINAL LIQUID INFUSER WITH INTEGRAL AGITATOR MEANS

(75) Inventors: Mark W. McGlothlin, San Diego, CA (US); Scott W. Herrick, San Diego, CA (US); Whitney A. Williams, Solana Beach, CA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1810 days.

(21) Appl. No.: 10/874,198

(22) Filed: Jun. 24, 2004

(51) Int. Cl.
*A61M 37/00* (2006.01)
(52) U.S. Cl. .......................................... 604/82
(58) Field of Classification Search .............. 604/82, 604/87–92, 131–132, 141–142; 128/DIG. 12
See application file for complete search history.

(56) References Cited

U.S. PATENT DOCUMENTS

| | | | |
|---|---|---|---|
| 3,087,707 A | 4/1963 | Moonan | |
| 3,718,235 A * | 2/1973 | Cronan | 222/136 |
| 4,640,623 A | 2/1987 | Tornell | |
| 4,641,974 A | 2/1987 | Church | |
| 4,858,759 A * | 8/1989 | Mauthe et al. | 206/221 |
| 4,928,857 A * | 5/1990 | Ecker | 222/211 |
| 5,080,652 A * | 1/1992 | Sancoff et al. | 604/132 |
| 5,135,497 A | 8/1992 | Hessel et al. | |
| 5,167,631 A | 12/1992 | Thompson et al. | |
| 5,207,320 A | 5/1993 | Allen | |
| 5,219,334 A * | 6/1993 | Tsukada | 604/132 |
| 5,246,670 A | 9/1993 | Haber et al. | |
| 5,263,935 A | 11/1993 | Hessel et al. | |
| 5,284,481 A | 2/1994 | Soika et al. | |
| 5,294,763 A * | 3/1994 | Chamberlain et al. | 219/729 |
| 5,354,278 A * | 10/1994 | Kriesel | 604/132 |
| 5,544,960 A | 8/1996 | Sommovigo et al. | |
| 6,063,058 A * | 5/2000 | Sakamoto | 604/132 |
| 6,103,139 A | 8/2000 | Kohout | |
| 6,406,276 B1 | 6/2002 | Normand et al. | |

* cited by examiner

*Primary Examiner* — Kevin C. Sirmons
*Assistant Examiner* — Andrew Gilbert
(74) *Attorney, Agent, or Firm* — Dority & Manning, P.A.

(57) ABSTRACT

An internal bladder agitator member(s), which are free to travel in the retained fluid when the bladders are in the filled state. When the bladders are not inflated, the agitator member(s) take up some of the free internal space of the bladder core, resulting in reduced retained fluid volume at the end of an infusion cycle. The free floating bladder agitator member(s) act in the dual role of elastomeric bladder support member(s) and agitator/mixer(s).

7 Claims, 8 Drawing Sheets

MEDICINAL LIQUID INFUSER WITH INTEGRAL AGITATOR MEANS

BACKGROUND OF THE INVENTION

This invention resides in the field of controlled liquid delivery devices, such as those used in the administration of medicaments. This invention primarily relates to such devices, which derive their infusion pressure from elastomeric bladders. The present invention further relates to such devices with a means of agitating or mixing liquids contained within their infusion bladder(s).

DESCRIPTION OF THE PRIOR ART

In the prior art various types of infusion devices have been proposed. For example, U.S. Pat. Nos. 5,080,652 to Sancoff, et al, 5,284,481 to Soika, et al, 5,263,935 to Hessel et al, 5,167,631 to Thompson et al, 5,135,497 to Hessel et al, and 6,406,276 to Normand et al, all of which disclose various devices that generate pressure within elastomeric bladder(s) to expel a liquid from a liquid delivery device.

All of the above cited patents utilize an outer casing or housing which is used to limit the expansion of the inflated elastomeric bladder. The housings are also useful in containing any potential spilled liquid in case of elastomeric bladder failure or leakage. Even in the case of hemispherical or spherical bladders, the use of an outer case is called for. Clearly, such outer housings are desirable when an elastomeric bladder is of a form other than a sphere. For instance, many elastomeric bladders are of a cylindrical form. During use, it is desirable to have these bladders inflate in a nearly spherical manner. The use of an outer casing or housing helps to achieve this goal by limiting the expansion of the cylinder in certain dimensions. When fully inflated, the bladders are generally not uniformly stretched in all dimensions. Spherical and hemispherical bladders come closest to being uniformly inflated.

Elastomerically powered infusion pumps are devices that eject liquid materials at continuous and prolonged rates by using pressure derived from the stretching of at least one elastomeric bladder. The elastomeric bladder contains liquid within its core, which is then forced out under pressure through an infusion set and subsequently into a patient. Flow rates of the infusion devices are controlled by methods well known to those skilled in the art, including, but not limited to the use of flow restrictive tubing, orifice restrictions, regulators, and the like. Pumps of this type are useful for the controlled delivery of drugs and other medications to patients, eliminating the need for periodic injections or other modes of administration, and avoiding the usual profile of a high initial concentration of the drug in the bloodstream followed by a gradual decline.

In general, infusion pumps are used to infuse liquid medicament or other beneficial liquid into ambulatory patients at a controlled rate. Such liquids include parenteral, enteral, diagnostic, chemotherapeutic, analgesics, local anesthesia agents, antibiotic, parenteral nutritional substances, anticoagulants and other beneficial liquids or suspensions. Other planned and potential future uses for such infusion devices include the infusion of the following types of fluids or suspensions, including, but not limited to: blood, stem and bone marrow cells, protein suspensions, lipid emulsions, monoclonal antibodies, gene vectors, DNA probes, and the like. Prominent among such devices are infusion pumps, in which released gas provides the driving force for the pressurized expulsion of liquid medicament or other beneficial liquid to an environment where the liquid has a beneficial effect. Also prominent among such devices are infusion pumps, in which the contraction of a previously stretched elastomeric bladder provides the driving force for the pressurized expulsion of liquid medicament or other beneficial liquid to an environment where the liquid has a beneficial effect. In these devices, the beneficial liquid is held in a bladder that contains at least one (preferably only one) opening.

One recognized issue associated with elastomeric infusion devices is the issue of overall size. Prior to use, infusion devices must be stored, generally within the confines of a pharmacy, where storage space is very limited. Sancoff (U.S. Pat. No. 5,080,652) and Soika (U.S. Pat. No. 5,284,481) recognize this issue, and address it in part by eliminating the need for a rigid shell over the bladder in an attempt to reduce their storage volume. Sancoff specifically introduces an improved infuser apparatus that contains a housing that is collapsible and/or reusable. However improved the Sancoff and Soika devices are, they retain a cylindrical shape for the infuser, which is not the most efficient geometrical configuration for storage purposes.

Thompson et al (U.S. Pat. No. 5,167,631) allows for the use of a generally spherical design, which is somewhat space efficient, but the use of a rigid outer shell negates the storage advantage for deflated infusion devices. A sphere is the most efficient means of storing a liquid, at least in terms of minimizing surface area for any given unit volume. However, the packing factor of spheres can be quite high compared to other geometrical shapes. Therefore, it would be desirable to have a housing that is collapsible and/or reusable.

Hessel et al (U.S. Pat. No. 5,135,497) teaches of the convenience of storing filled infuser bladders in the frozen state. The liquid to be infused needs to be thawed prior to use, which Hessel et al discloses is difficult to do with a spherical infusion bladder. Hessel et al states " . . . if the liquid to be infused is stored in a frozen state, an excessive amount of time would be required to thaw the liquid prior to dispensing because of the small surface area of the liquid". Hessel et al clearly recognizes the advantage of using a sphere to store large volumes of liquids efficiently, but dismisses the idea at least in part due to difficulties in thawing the frozen liquids. Instead, Hessel et al discloses a helical bladder design, which has the disadvantage of consuming a fairly large amount of storage space prior to use.

If the beneficial liquid is to be infused parenterally, it is very important not to inadvertently infuse any air into patients along with the liquid, as this can be damaging to the patient. Thus, infusion devices are designed in such as way as to prevent the administration of air. This is done by eliminating air from the fluid path of the infusion device prior to the start of infusion. Any residual air is generally eliminated by a hydrophobic air-eliminating filter, which is attached to the infusion set.

With liquids to be infused which are not true solutions, it is very important to have the suspended or dispersed ingredients homogeneously mixed immediately prior to infusion. In a similar manner, when thawing a previously frozen liquid in the bladder core, it is desirable to have an effective means of mixing to promote rapid thawing, even in the case of true solutions. Prior art infusion devices fall short in this area. With the elimination of air from the core of the infuser bladder prior to the start of infusion, it is difficult to actively keep the beneficial liquid homogeneously mixed throughout the infusion cycle. Thus, it is possible to have suspended materials separate during the course of the infusion cycle, which is highly undesirable.

Retained volume is the amount of fluid left in the infusion device at the conclusion of the infusion cycle. It is highly desirable to minimize the retained volume, so as not to waste valuable infusible liquid. Prior to infusion, the infusion device's bladder is filled with fluid, and subsequently allowed to infuse into the patient at a constant rate. Many infuser designs have a fixed mandrel or other support means (hereinafter referred to as "support member(s)") in the lumen or core of the bladder to take up internal bladder volume at the end of the infusion cycle, thus reducing retained volume. Infusion devices, which provide for retention of stress in the membrane at the conclusion of the fluid administration generally are able to remain in flush contact with the internal bladder support member(s), and therefore tend to have minimal retained volume. It is believed that all prior art elastomeric infusion devices have their support member(s) fixed in place relative to the bladders they are designed to support. In fact, the bladders are securely fixed to their support members. Because of this design limitation, the support member(s) cannot be used to effectively aid in the mixing or agitating of the liquid contained in the bladder. It is believed there are no prior art infusion devices which contain any free floating object(s) in their core(s) of the infusion bladder of infusion devices that can contribute to the mixing or agitation of the core liquid.

Numerous patents have issued on inventions relating to mixing means within fixed volume closed vessels, which do not relate to infusion devices. Representative examples are U.S. Pat. Nos. 3,087,707 to Moonan, 5,544,960 to Sommovigo et al, 4,640,623 to Tornell, 4,641,974 to Church, 5,207,320 to Allen, and 5,246,670 to Haber et al.

Moonan discloses the use of an agitating means for aerosol spray cans, which incorporates the use of free moving balls to facilitate the agitation of paint components, which may settle to the bottom of spray paint cans over time. By shaking the paint can, the balls agitate the core liquid. Moonan makes no reference to the use of such agitator balls in medical infusion devices, or in the use of the balls to compensate for retained volume in any sort of infusion or dispensing article. Sommovigo et al discloses similar balls, which are used for agitation of the core fluid. Tornell discloses the use of modified spherical agitator balls for use in sealed spray containers. By adding a number of ribs to the surface of the spheres, additional agitation is possible. The ribs are preferably formed from wire stock, providing for fluid communication with the interior of the spherical balls. Because these wire forms can contain beneficial liquid, they are not useful in reducing retained volume in elastomeric infusion devices. Tornell does not disclose the use of such agitators for injectable or other medical fluids. Church discloses an unbalanced free-floating agitator for an aerosol can. The geometry of the agitator does not allow for a low retained volume, nor is there a disclosure of its utility for use in medical fluids. Haber et al discloses a hollow sphere fabricated from glass, ceramic, inert plastic, such as polypropylene, polyethylene, used to gently agitate the suspended contents of a specific type of drug-containing vial. The sole purpose of the bead is for gentle agitation of the contents. Allen discloses the use of a ceramic bead used in a three-compartment ampule, which contains components of a liquid pharmaceutical preparation. The purpose of the bead is not to mix or agitate the contents of the ampule, but to provide an indication of the seal integrity.

It is often desirable to infuse parenteral solutions at or near body temperature. Prior to use, the liquid contents of infusion devices can be heated in a number of ways. One preferred way is to apply microwave energy to the bladder core of the infusion device by placing the pump in a conventional microwave oven prior to use. This can warm and/or melt the contents in the bladder core. Not all fluids can safely be subjected to microwave radiation, so it is often necessary to just let the devices warm up by conventional. U.S. Pat. No. 6,103,139 to Kohout discloses an encapsulated hot pack activator system, which produces heat on demand by liberating the latent heat of fusion from a super-cooled liquid, useful in the manufacture of hot packs. Kohout does not disclose the use of this sort of device for heating medicinal fluids.

SUMMARY OF THE INVENTION

The present invention is directed to an infuser that overcomes some of the specific deficiencies of prior art infusion devices, including the difficulty in mixing the contents of the infuser bladder(s) prior to and/or during the infusion cycle. The invention also helps to overcome the difficultly involved in thawing and or rapidly heating the contents of a frozen infuser. The present invention addresses the need to add heat to the fluid over the course of the infusion cycle.

The present invention consists of internal bladder support member(s), which may be in the form of cylindrical or cylindrical capsule mandrels, hollow or solid spheres, ellipsoids or the like. Such support member(s) are free to travel freely in the retained fluid when the bladders are in the filled state. When the bladders are not inflated, the support member(s) take up some, and preferable more than 50%, more preferably more than 75% and most preferably more than 90% of the free internal space of the bladder core, resulting in reduced retained fluid volume at the end of an infusion cycle. Free floating mixing ball(s), or the like, act in the dual role of elastomeric bladder support member(s) and agitator/mixer(s). Agitator balls can also be added adjunctively to the fixed support member(s) of existing designs of elastomeric infusers to aid in fluid mixing and re-suspension, while further reducing retained fluid volume. An alternative embodiment provides for the addition of mixing balls or other agitators into any existing infusion pump design to provide for improved agitation.

It is an object of the present invention to provide a new and improved infusion device.

It is an object of the present invention to provide a new and improved infusion device that can be efficiently stored.

It is an object of the present invention to provide a new and improved infusion device that overcomes the difficultly involved in thawing and or rapidly heating the contents of a frozen infuser.

It is an object of the present invention to provide a new and improved infusion device that aids in fluid mixing and re-suspension, while further reducing retained fluid volume.

These and other objects and advantages of the present invention will be fully apparent from the following description, when taken in connection with the annexed drawings.

DESCRIPTION OF THE PREFERRED EMBODIMENT

Figure 1:
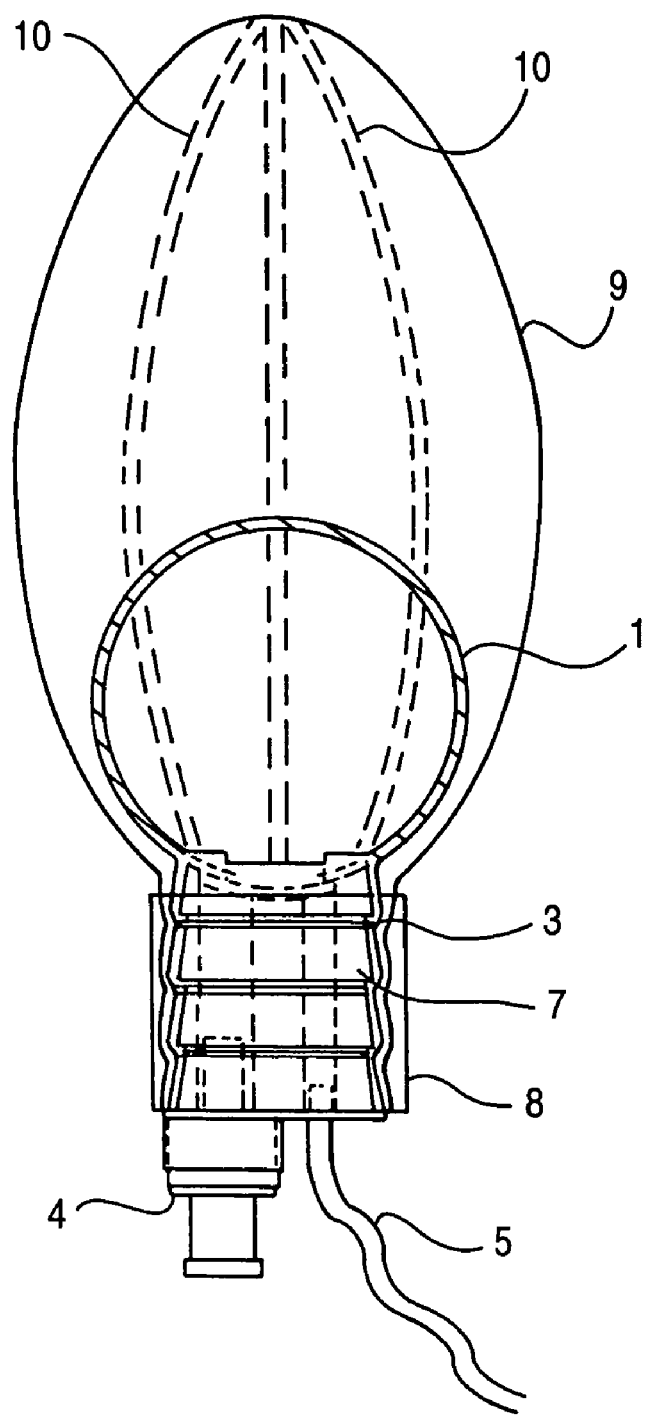
FIG. 1 is a side elevation cut away view of an infusion device in accordance with the present invention.
Figure 2:
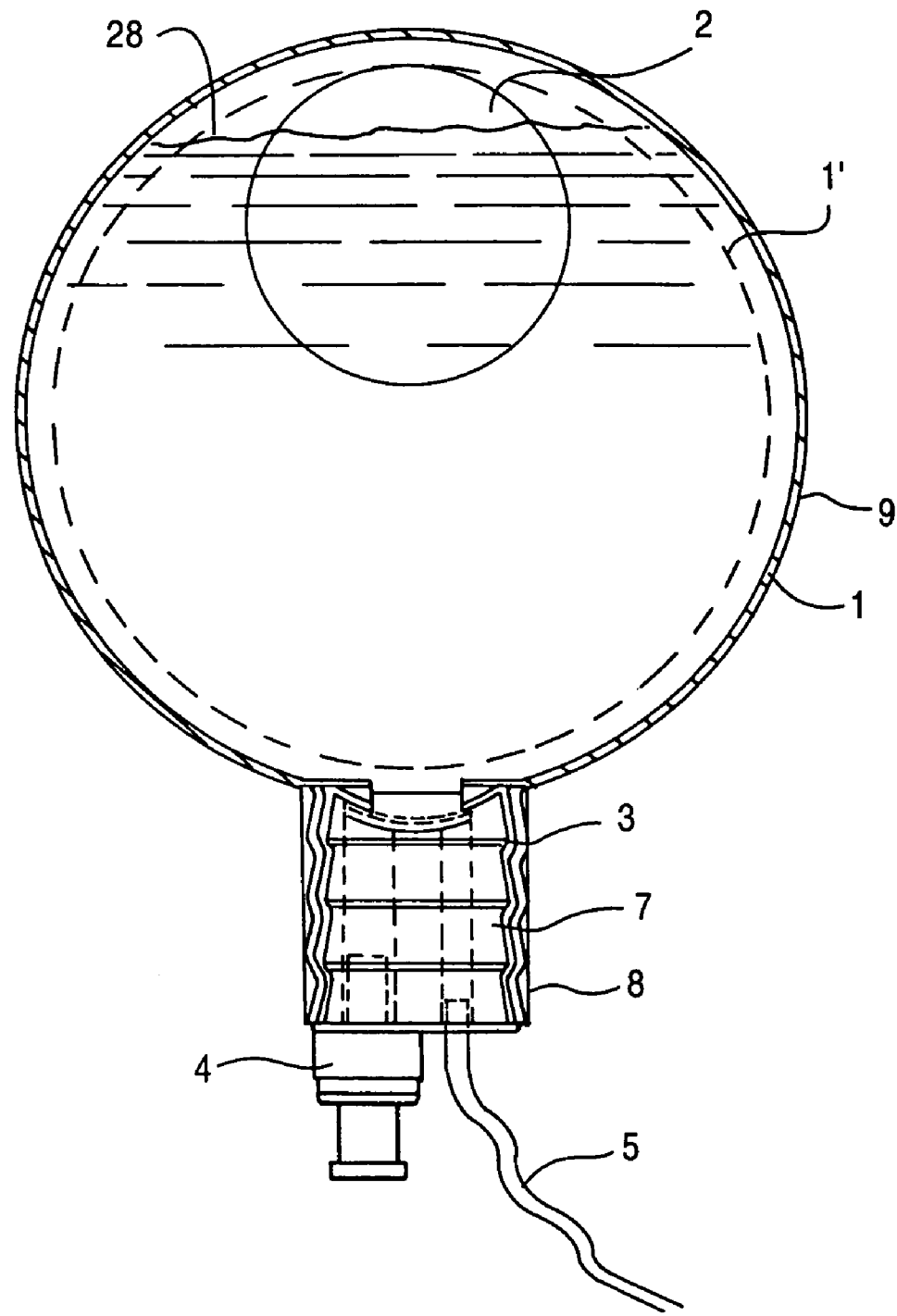
FIG. 2 is a side elevation cut away view of an infusion device in accordance with the present invention, which uses a spherical bladder support.

Referring now to the drawings in greater detail, FIG. 1 shows The most preferred configuration is that of a generally spherically shaped elastomeric infuser, with a generally spherical, free floating ball or agitator (shown in FIG. 2). The ball has the dual functions of facilitating mixing and taking minimizing retained volume. Such spherical member(s)s can contain convulsions, flutes, dimples, or the like to aid in agitating efficiency. Wire form support member(s) can also be used, but at the cost of being able to maximally reduce the retained volume. Small beads or other shaped articles can be used internally in the wire forms to minimize the retained volume to a considerable extent. The agitator member(s) can be made either positively or negatively buoyant to aid in agitating efficiency. Alternately, they can be made neutrally buoyant to reduce the shear forces the beneficial liquid is subjected during mixing. Other geometric configurations can also be used effectively, including generally cylindrical shapes, cylindrical capsule shaped, ellipsoid shapes, cubes, pyramidal and other geometric forms. Hollow, solid, and foam constructions are possible. The agitator member(s) can have specific gravities of one, less than one, or more than one can be utilized. The use of using agitator member(s) with specially tailored specific gravities allows the agitator member(s) to float, sink or remain neutrally buoyant.

Multiple shapes can also be used to increase mixing efficiency, but at the expense of some excess retained volume. Large numbers of very small spheres or other shapes can be used, and will readily form into the shape of the bladder, when the bladder is in the mostly deflated configuration. This use of multiple spheres or the like can result in very efficient mixing, although at the expense of some retained volume. When using multiple spheres, it is desirable to use a configuration, which yields a very high packing volume ratio. When the bladder is deflated, it is assumed that all of the spheres are in contact with one another. This condition is referred to as "close packing". In the least efficient close packing form, simple cubic packing (SCP), it can be shown that the spheres fill 52% of the total volume of a sample. In the most efficient close packing arrangement, cubic close packing (CCP), solids fill 74% of the total sample volume. To increase the efficiency of packing, spheres or other shapes of dimensions small enough to fill in the interstitial spaces between the packed spheres can be used. From this, it is clear that some amount of retained volume will have to be increased to accommodate multiple agitator member(s).

It is also possible to have multiple agitator members, which define a singe geometrical form. For instance, two hemispheres can be used to form a sphere. Four small cubes can be used to form a larger cube, etc. The use of two hemispheres is particularly preferred, and the two readily form into one sphere, allowing for greater agitator functionality, while maintaining a very small-retained volume. If desired, one or more tethers can be used to allow for a single sphere or the like to spread into multiple pieces when shaken vigorously, yet has the propensity to come back into its original form once the shaking subsides. This configuration allows for very good mixing efficiency while maintaining the ability to minimize retained fluid volume.

Optionally, the support member(s) can actively contribute to the heating and/or thawing of the fluid prior to infusion. In certain instances it is advantageous to infuse fluid at temperatures above room temperature, yet not greatly exceeding body temperature. Cold fluid administration can be uncomfortable for patients. One particularly preferred method of adding heat on a continuous basis during the infusion process is to add a super-cooled liquid, along with a nucleation site generator, such as the combination described in U.S. Pat. No. 6,103,139 (Kohout) to the core of an otherwise hollow, flexible support member. Prior to infusion, manual means can be used to activate the nucleation means, thus providing an active heating source to the beneficial fluid via the liberation of the latent heat of fusion over an extended period of time. Another means is to fabricate the support member(s) from material(s), which have a large heat capacity, such as solid ceramic, aluminum, and the like. Other known means of producing local heating can also be used to generate heat in the core of the support member(s) during the infusion cycle. Such heating methods are well know by those skilled in the field of hand warmers, chemical heat packs, and the like.

Optionally, the agitator member(s) can be made from or contain a material which is especially good at converting microwave energy to heat energy. Such devices materials are generally known as microwave susceptors, several types of which are disclosed in U.S. Pat. No. 6,534,755 (Paulucci), which is incorporated in its entirety by reference. The cold or frozen infuser can then be inserted into a microwave oven prior to use to facilitate warming and/or thawing of the beneficial fluid. With the use of intermittent shaking between microwave oven cycles, the frozen core material can be quickly and efficiently thawed out. The use of the microwave susceptors allows the frozen fluid to preferentially melt at the interface of the surface of any or all of the support members. This allows for the use of effective agitation means earlier in the thawing cycle than would be possible otherwise. This overcomes the limitation of the spherical shaped infusion device cited in Hessel.

A spherically shaped detached agitator member can be made at different densities, as needed. Strongly positively or negatively buoyant agitator member(s) are the most efficient as agitators for the core fluid. Strongly negatively buoyant agitator members are most preferred. In the case of a substantially negatively buoyant spherical support member, the detached sphere can also be used to help dislodge air bubbles from the sidewalls of the interior of the infusion bladder by rotating the sphere around the interior wall of the filled infuser bladder. This can help to dislodge trace quantities of air prior to infusion.

Optionally, if a spherical agitator member is used, it can be made in a such a way that it has an offset center of gravity, which will make the support member(s) oscillate in an accentuated and erratic manner when the infuser is shaken. Such oscillations and/or movements increase the efficiency of agitation.

In the case of the most preferred spherical support member, it is important to make certain that the surface of the support member does not seat in a flush manner to the fluid exit port. Such seating can be prevented by putting some form of standoff mechanism on the outlet portion of the infusion device housing. Non-limiting examples of such stand offs include groves, fins, and divots. Similar stand off means can be affixed to or incorporated in the design of the spherical support member. Combinations of the foregoing can also be used. Essentially any configuration, which allows for an open fluid communication path to the infusion set, is acceptable.

The elastomeric bladder can be made from various elastomeric materials. Preferred elastomeric bladders include those made of cross-linked synthetic polyisoprene, cross-linked poly dimethyl silicone, and those made from natural rubber. Thermoplastic vulcanizates are also preferred. Thermoplastic elastomers are less preferred, but are acceptable. In the case of natural rubber bladders, it is desirable to include a barrier layer or additional non-rubber liner to prevent direct contact of the natural rubber and the beneficial fluid in order to prevent latex allergy reactions. The most preferred material is synthetic polyisoprene formed by the anode dipping method and cured with an organic peroxide curing system. The dip molding process allows for the production of a nearly uniform wall thickness bladder. Spherical bladders are highly preferred, in that they uniformly expand and contract, and maintain constant infusion pressure over a wide range of fill volumes.

The collapsible housing can be made from any number of elastomeric materials. The collapsible housing is preferably made from a blow molded or dip molded housing approximately 0.0085" in thickness and made of a material such as polyurethane, PVC, polyethylene, synthetic polyisoprene, styrene butadiene, and most preferable a blend of synthetic polyisoprene and styrene butadiene. This forms a simple inexpensive compact unit with a certain amount of protection for the elastic reservoir.

Optionally, one or more bladders can be assembled, one inside the next, into multiple layers to reduce the probability of liquid leaking out during use. For a leak to occur, all of the bladders would have to have one or more holes. The probability of having a leak decreases substantially as the number of bladder layers increases. Additionally, should there be a catastrophic failure of less than the total number of bladders used, then the liquid contents would still be contained. The optional use of an outer shell or housing can also act to catch any leaking liquid if additional protection is desired.

Figure 8A:
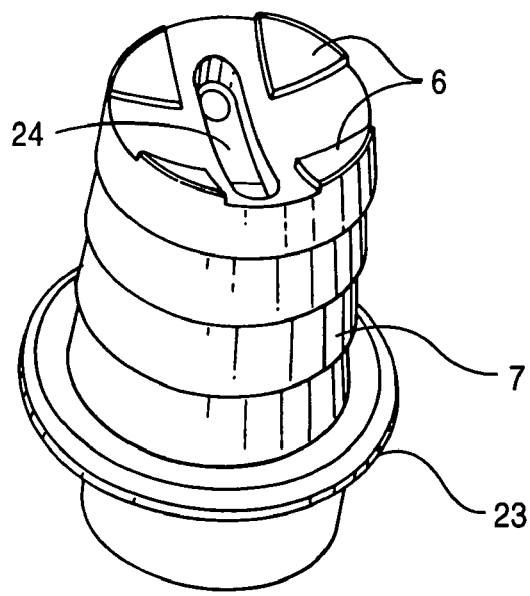
FIG. 8A is a perspective view of the barbed mandrel from the top.

FIG. 1 illustrates an infusion device constructed in accordance with the present invention. The device has a barbed mandrel 7, which is secured to a housing 9. The housing may be transparent. A fluid tight seal is made by placing the neck of the bladder over one or more of the barbs. Since the bladder neck is elastomeric, it conforms tightly, under elastic stress, to the barbs, further helping the formation of a fluid tight seal. A deflated elastomeric infusion bladder 1 is positioned next to a standoff 6 within the housing 9 (see FIG. 8A). Filament wrappings 3 are wrapped around the bladder neck after it is placed on the barbed mandrel 7. The filament wrappings are preferably high molecular weight polyethylene threads that are wrapped around the outside of the elastomeric bladder neck to further secure the fluid tight seal created by stretching the bladder neck over the barbs. The threads are especially helpful if high pressure is used in the bladder where the elasticity of the bladder neck is not sufficient to maintain a fluid tight seal between the bladder neck and the barbed mandrel when the bladder is in a pressurized state. A one way filling port 4 and a conventional flow restrictive administration set 5, for infusion of liquid into a patient, are secured to the bottom of the mandrel 7 in any conventional manner.

The barbed mandrel 7 contains a standoff 6, which prevents the occlusion of the fluid path during use, as will be explained more fully below. The beneficial liquid 28 (see FIG. 2) is contained in the bladder 1 after being introduced through the port 4. The housing 9 may have a plurality of flutes 10 (shown in dotted lines in FIG. 1) secured to the inside of the housing, in any conventional manner. The flutes 10 aid in the expansion of the bladder 1 into a sphere. The housing 9 is a resilient membrane that is essentially a collapsed sphere (similar to an inflatable beach ball). When inflated, in this case when the elastomeric bladder inside the housing is inflated, the flutes expand and flatten out to form the shape of a sphere. The fluted housing does not actually aid in the expansion of the elastomeric bladder into a sphere. The elastomeric bladder, starting as a sphere naturally expands into a sphere. The outer fluted housing, being flexible, will conform to any shape the elastomeric bladder takes. The housing tends to protect the bladder from being punctured by extraneous objects that might come into contact with the infusion device during use. Further, in the unlikely event of bladder rupture, the contents of the bladder can be contained by the housing.

FIG. 2 shows the infusion device of FIG. 1 in a fluid filled, bladder inflated configuration. The flutes 10 are not shown in FIG. 2 for clarity.

Element 8 is a piece of heat shrink tubing that is placed over the attachment points of the housing and bladder to the mandrel. It is shown in an expanded state in FIG. 1, and in a shrunken state in FIG. 2. When shrunk down heat shrink tube 8 will additionally secure the attachment of the housing and bladder to the mandrel, and will improve the aesthetics of the attachment area.

The infusion device of the type illustrated by FIGS. 1 and 2 is operated by filling the beneficial liquid 28 into the bladder 1, through a one-way valve 4. The inflated bladder 1 causes the liquid in the bladder to be pressurized since the bladder will tend to return to the shape of FIG. 1. At least one agitator member 2 is placed within the bladder 1. The agitator member 2 will agitate the liquid when the bladder 1 is shaken or rotated. During use, the fluid from the bladder is injected into the patient via a venous catheter (not shown) connected to the flow restrictive tubing 5. At the conclusion of the infusion, the infusion device will return to the configuration shown in FIG. 1. The retained volume of this infusion device is very small. Also, additional bladders 1' can be inserted, one within the other, with the fluid contained within the inner most bladder, in order to minimize leaks. It should be understood that although only one additional bladder 1' is shown in FIG. 2, any number of additional bladders can be used without departing from the scope of the invention.

Figure 3:
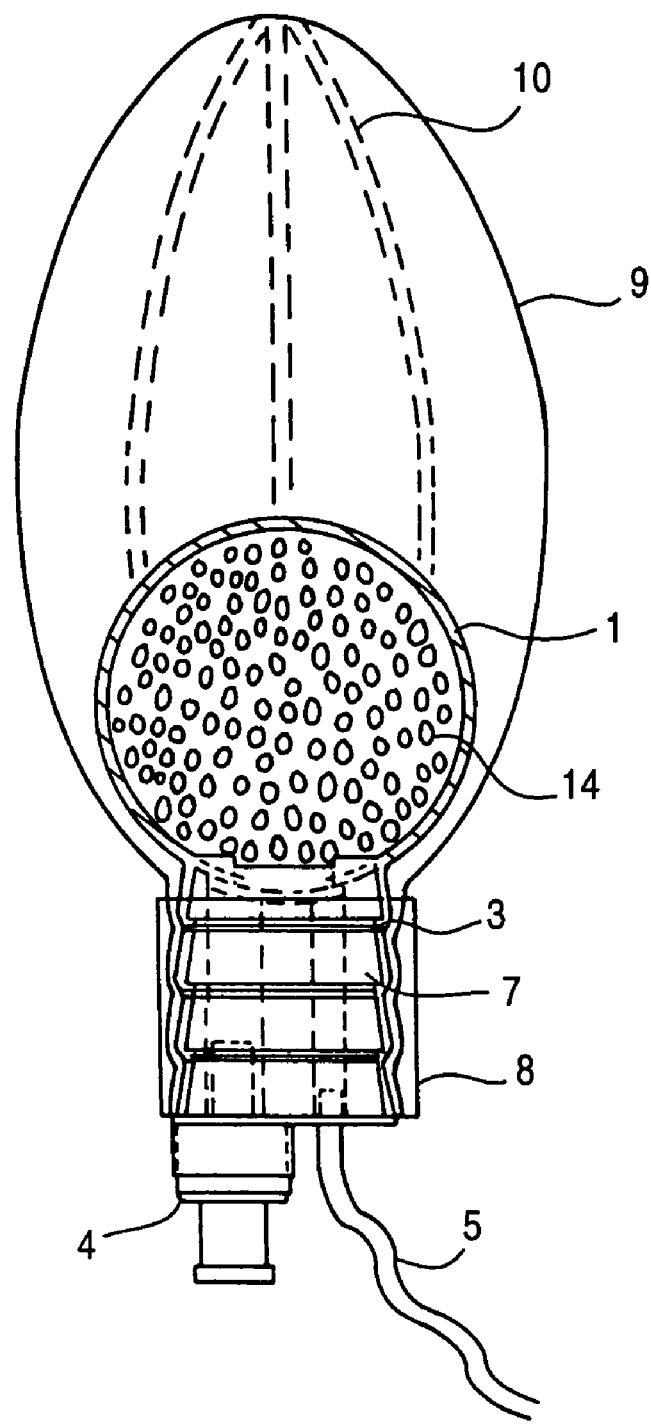
FIG. 3 is a side elevation cut away view of an infusion device in accordance with the present invention in the bladder deflated position.

FIG. 3 shows a similar infusion device to the device shown in FIGS. 1 and 2. The spherical agitator is formed of a plurality of spheres 14, made of hard plastic. The beneficial fluid can fill the interstitial spaces between the small spheres, yet the retained volume is still reduced, as compared to no agitator member(s). During inflation of the bladder 1, the spheres 14 are free to travel throughout the core fluid since there will be more space within the bladder 1. The free movement of the spheres 14 will also aid in mixing of the fluid. At the conclusion of the infusion cycle, the spheres resume their collective spherical configuration due to the pressure exerted by the infusion bladder.

Figure 4:
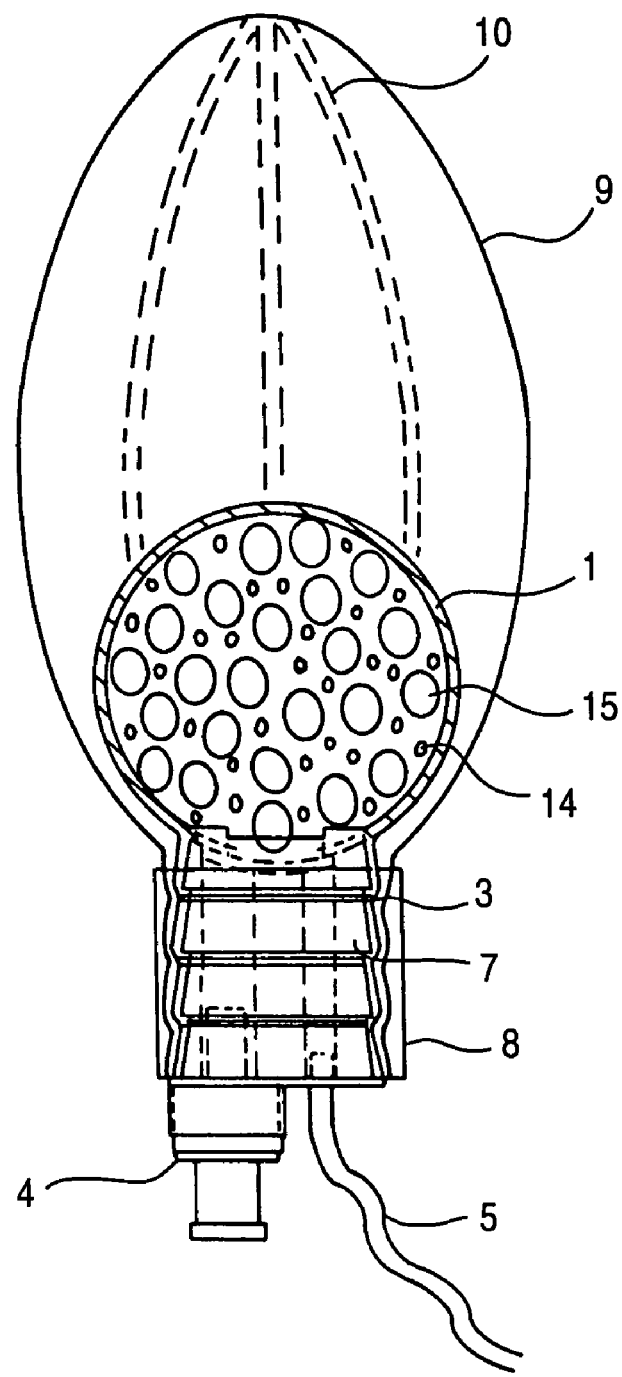
FIG. 4 is a side elevation cut away view of an infusion device in accordance with the present invention in the bladder deflated position.

FIG. 4 shows an infusion device similar to the device of FIG. 3. Spheres 15 consume much of the retained volume within the bladder 1, while yet smaller spheres 14 fill in some of the interstitial spaces formed between the spheres 15. The function of this infusion bladder is virtually identical to the device of FIG. 3, except that there is less residual volume of fluid.

Figure 5:
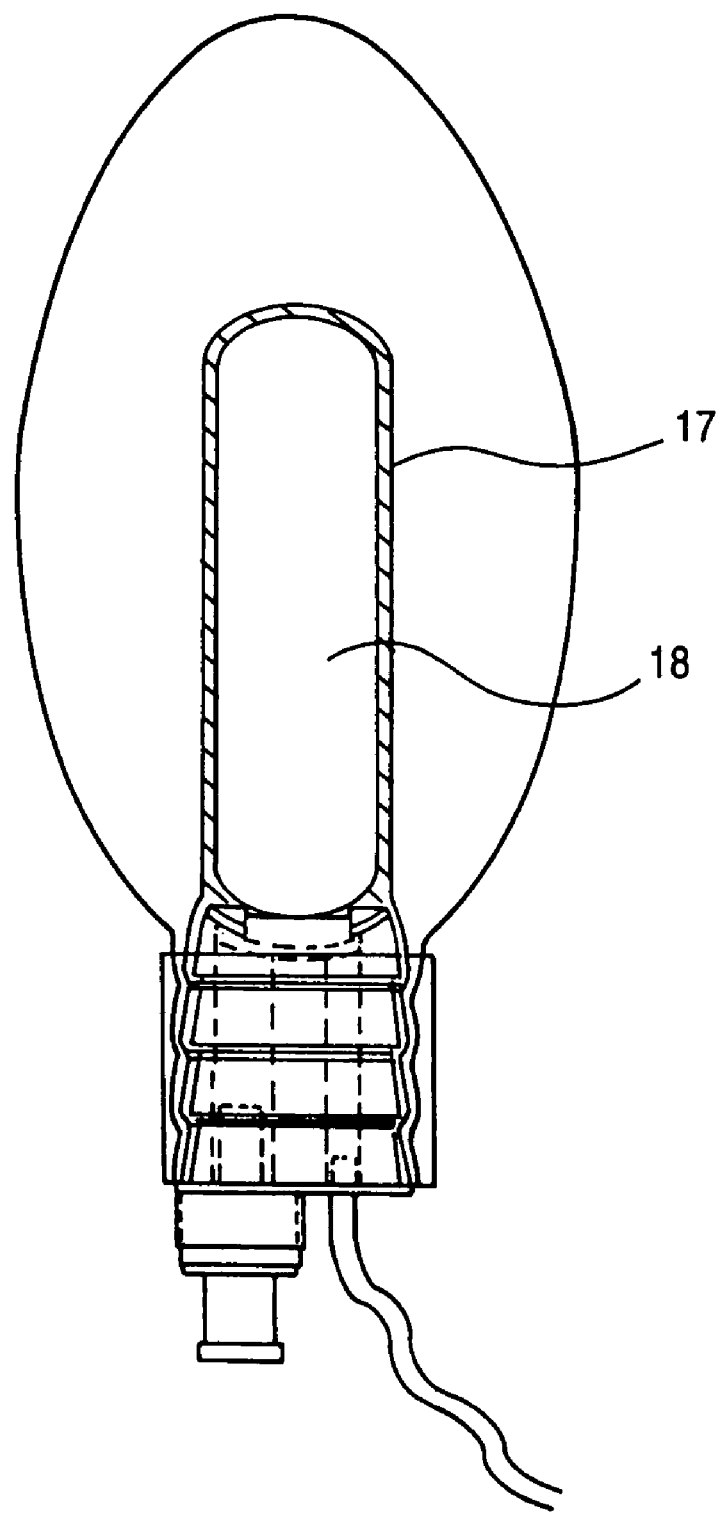
FIG. 5 is a side elevation cut away view of an infusion device in accordance with the present invention in the bladder deflated position.

FIG. 5 depicts an infusion device containing an agitator member 18, with a cylindrical form. The elastomeric bladder 17 is of a complimentary form. The cylindrical capsule shaped agitator can be used as an agitator, as in other embodiments of this invention. When the bladder 17 is expanded by the introduction of fluid, the volume of the bladder will be larger than the volume of the support member 18. This will allow the agitator member to move within the liquid and to agitate the liquid.

Figure 6:
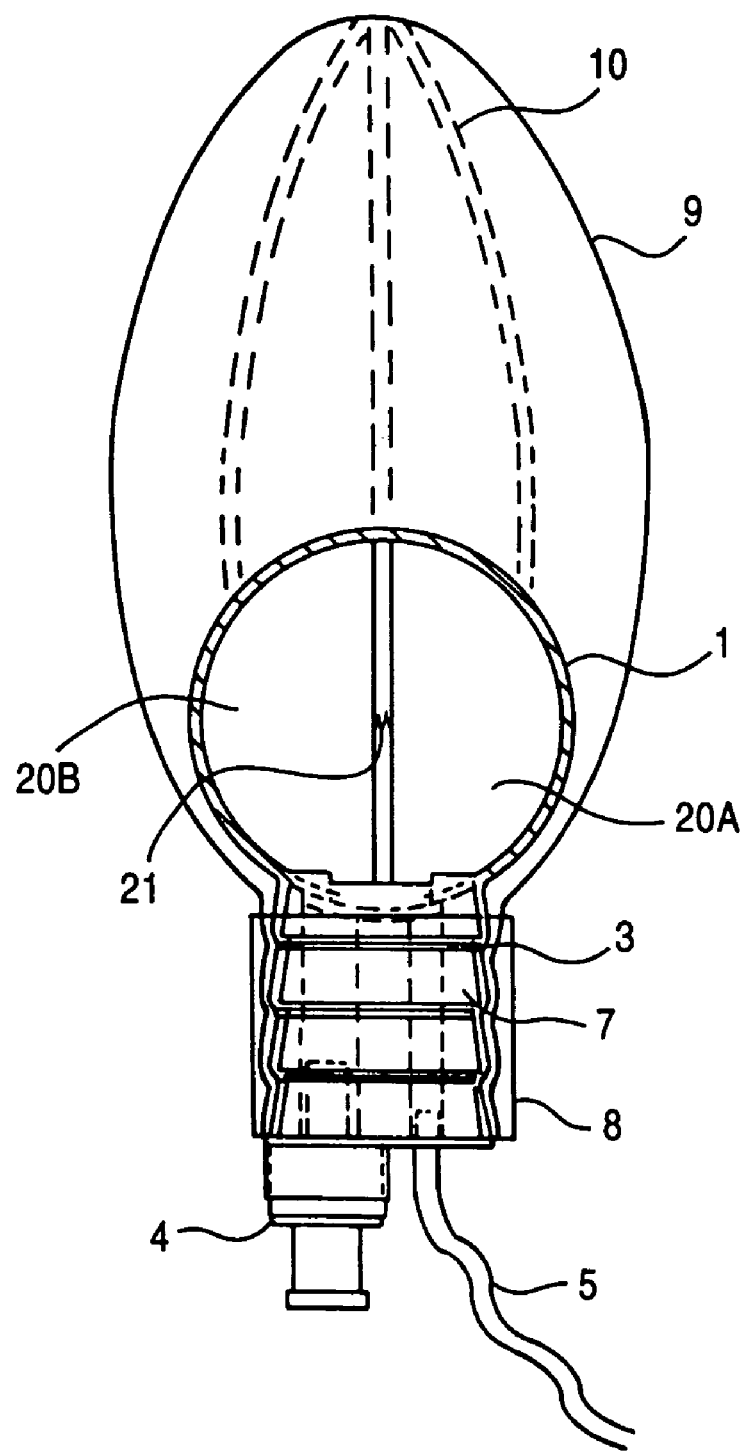
FIG. 6 is a side elevation cut away view of an infusion device in accordance with the present invention in the bladder deflated position.
Figure 7:
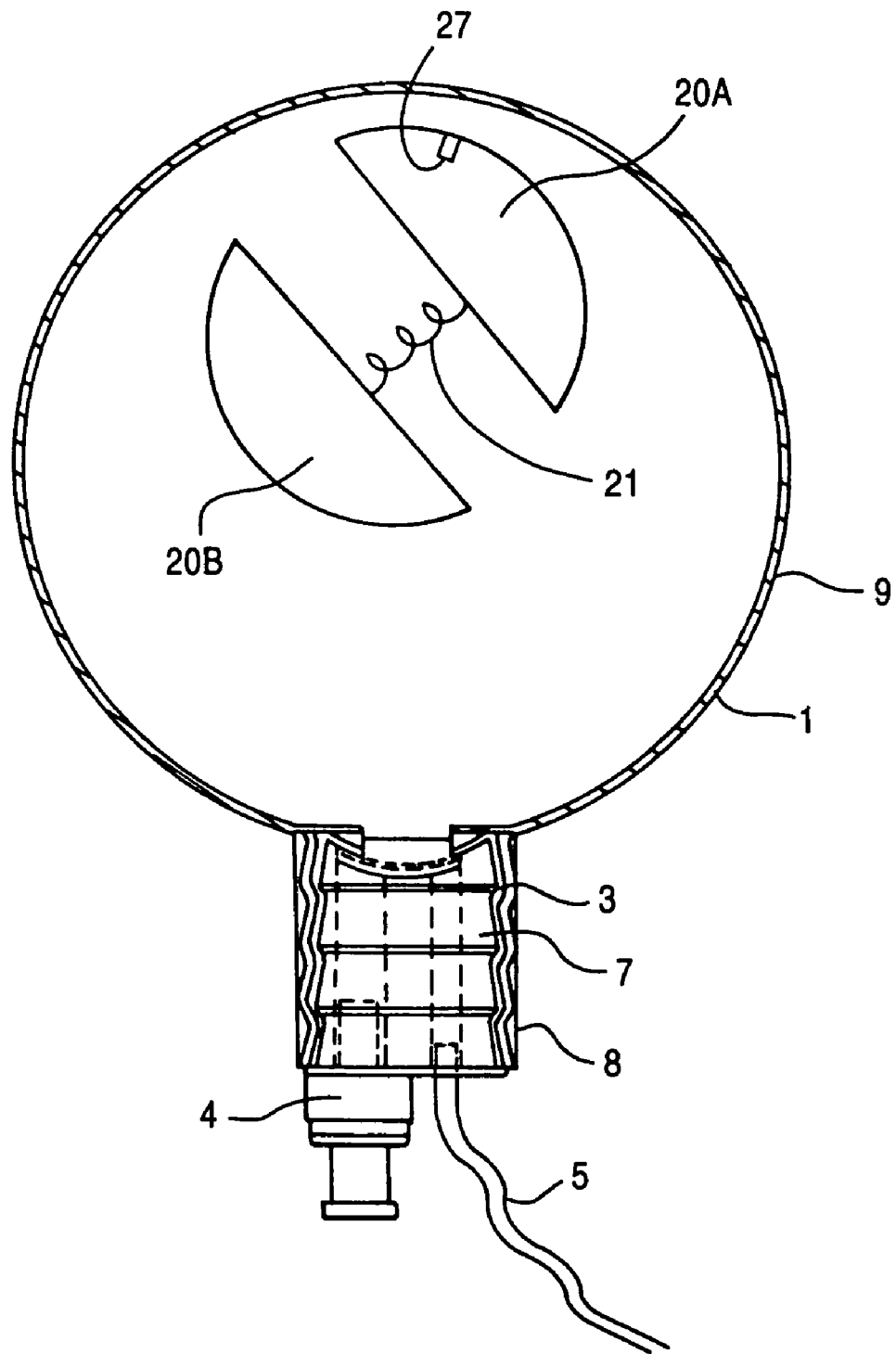
FIG. 7 is a side elevation cut away view of an infusion device in accordance with the present invention in the bladder-inflated position.

FIG. 6 shows an infusion device in the bladder deflated position. An elastic tether 21 is shown in the collapsed position, keeping hemispheres 20A and 20B together. FIG. 7 shows the same infusion device in the bladder inflated position, with the elastic tether 21 in an elongated position. When filled with fluid and shaken, hemispheres 20A and 20B will separate, yet tether 21 pulls them back into a combined spherical configuration while not being agitated. One or more of the hemispheres could contain a weight 27 which will change the center of gravity of the hemisphere and this will aid in the agitation of the liquid. Other methods of changing the center of gravity could be used such as making one portion of the hemisphere bigger than another portion of the hemisphere. In addition, the same changes could be made to the agitators of FIGS. 2, 3, 4, and 5. In addition the agitators could be made hollow or solid.

The specific gravity of the agitators could be made greater than 1 so they sink in the liquid, or they could be made the same as the liquid so they float. While spherical agitators are preferred, other shapes such as, but not limited to, cylindrical, ellipsoidal or pyramidal could be used without departing from the scope of the invention. The amount of volume of the agitators relative to the volume of the bladder can be adjusted so the agitators take up 74% or more of the volume of the bladders.

EXAMPLE 1

Demonstration of Improved Mixing

Molding of the Elastomeric Bladder

In this example, a two layer, laminated bladder was constructed. The innermost layer of the laminated structure was made by means of dip molding synthetic polyisoprene (a synthetic rubber), Natsyn 2200 (Goodyear Chemical, Akron, Ohio) containing 1.5 phr of the Dicumyl Peroxide (RT Vanderbilt Company Inc., Norwalk, Conn.), 5 phr CAB-O-SIL M-5 Amorphous Fumed Silica (Cabot Corporation, Boston, Mass.) and an antioxidant. The outer laminated layer was made by a dip molding process from synthetic polyisoprene latex, Kraton IR-401 (Kraton Polymers, Houston, Tex.), containing a peroxide cross linking agent, 10 phr fumed silica content, Cab-O-Sperse GP-50 Silica Dispersion from Cabot Corporation, Boston, Mass., a surfactant, and an antioxidant. After drying of both laminated layers, the bladder was allowed to cross-link in a molten salt in accordance with the methods taught in U.S. Pat. No. 6,569,375. The resultant bladder was spherical and of a generally uniform wall thickness of about 0.0295"+/−0.002. The internal diameter of the spherical portion of the bladder was about 1.25 inches.
Assembly of the Infusion Device The elastomeric bladder was then combined with other components to form an infusion device, which resembles the device depicted in FIGS. 1 and 2. In this configuration, the infusion device contains a 1.25" diameter ball as the spherical support member. The ball was fabricated by an injection molding process using K-Resin material, KR-1, (Chevron Phillips Chemical Company LP, The Woodlands, Tex.) a styrene-butadiene copolymer (SBC). When the ball was placed into the bladder, the internal surfaces of the bladder conform to the outside diameter of the glass ball, allowing for essentially no residual volume of fluid to remain in the deflated state. The open stem end of the bladder was secured in place by means of a wrapped suture to the barbed mandrel 7 of FIG. 1. The barbed mandrel was fabricated by an injection molding process from K-Resin material, KR-1, a styrene-butadiene copolymer (SBC). The elastomeric bladder was attached to the barbed mandrel by securely tying the stem portion of the bladder down to the barbed mandrel with Tensylon rounded thread from E.M. Threads, Inc. (Monroe, N.C.).

Figure 8B:
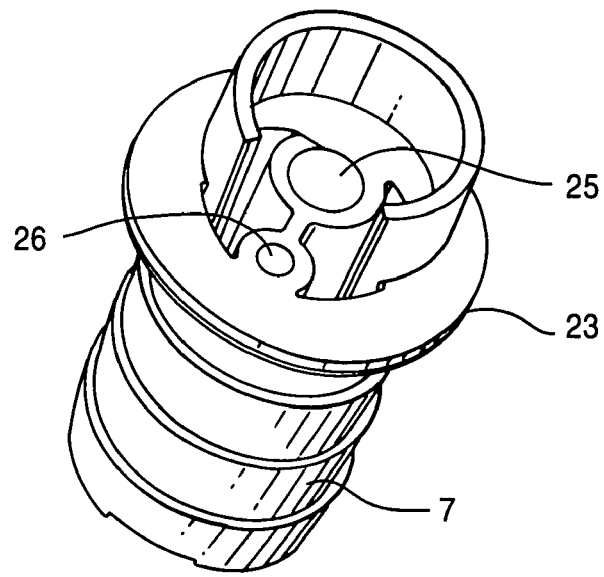
FIG. 8B is a perspective view of the barbed mandrel from the bottom.

The end of the barbed mandrel 7 has raised offsets 6 (see FIG. 8A), which prevent the agitator member 2 (in FIG. 2), 14, 15 (in FIGS. 3 and 4), 18 (in FIGS. 5) and 20A, 20B (in FIG. 6) from seating in such an orientation that it would block the aperture 24 (see FIG. 8A) leading to infusion fluid discharge port 26 (see FIG. 8B). This allows for a constant fluid passage channel even when the agitator member was firmly pressed against the top of the barbed mandrel. These raised offsets 6 circumscribe a single discharge hole 24, which is in fluid communication with both an inlet 25 and outlet port 26 on the opposite end of the barbed mandrel. The inlet port has a female luer opening allowing for placement of a one-way filling valve.

In this example, the one-way valve 4 contains a female luer-lock inlet and a male luer outlet and was made of a rigid poly vinyl chloride-bodied valve with a silicone stem and polypropylene plug, commercially available from Qosina Corporation, Edgewood, N.Y. This valve allows for easy filling of the infusion device with the fluid to be infused via a standard syringe or other comparable device having a male luer-lock fitting. The exit port of the mandrel was a straight hole of 0.088" diameter into which a polyvinyl chloride flexible infusion set was solvent bonded into place.
Filling of the Infusion Device A quantity of 0.5 grams of solid dextrose was placed in the bladder 1. The dextrose was lodged between the spherical ball 2 and the inside diameter of the infusion bladder. A quantity of 9.5 ml of deionized water was injected into the bladder via the fill valve 4 and came into contact with the dextrose. The infusion device was vigorously shaken until all of the dextrose was dissolved to the point that only a clear liquid was observed. The time for this complete dissolution was noted, which was 121 seconds.

COMPARATIVE EXAMPLE 1

The assembly and dissolution testing procedure of Example 1 was preformed, except that no support member 2 was used in the assembly of the infusion device. The infusion bladder was simply an empty space. Again, 0.5 grams of solid dextrose was added to the core of the bladder, followed by the addition of 9.5 grams of deionized water. After the addition of the water, the infusion device was vigorously shaken until all of the dextrose was dissolved. The time for dissolution in this case was 208 seconds.

EXAMPLE 2

Demonstration of the Advantage of the Preferred Embodiment with Respect to Improved Thawing The fabricated infusion device of Example 1 was filled with 50 ml of deionized water and placed in a freezer at 0 degrees F. for 4 hours, at which time all of the water was frozen. A second infusion device (control device) was made in a manner similar to that of Example 1, but was constructed without the support 2, and was similarly filled with 50 ml of deionized water and placed in a freezer for 4 hours, at which time all of the water was frozen. Both infusion devices were subsequently placed in a microwave oven, (Sharp Corporation Carousel II for 2 minutes on high-power setting). After the two minutes of heating, the infusion devices were removed and agitated for 15 seconds by vigorous manual shaking. Observations were recorded, and the infusion devices were placed back into microwave oven for 1 minute on the high power setting. The devices were again removed and agitated for 15 seconds. Observations were recorded. This procedure was repeated until both elastomeric membranes were completely thawed. See table 1 for experimental date.

TABLE 1

Experiment Data

| Infusion Device | Time For Dissolution, seconds, |
|---|---|
| Inventive Embodiment - with agitator means | 135 |
| Control - No agitator means | 165 |

As can be seen, the present invention offers an advantage with respect to thawing time, as compared to the control, which is representative of the prior art. In addition, the agitators can be made from a material that can be easily heated by microwaves called microwave susceptors.

EXAMPLE 3

An elastomeric infusion device, the Home Pump Eclipse TM (I-Flow Corporation, Lake Forest, Calif.) was disassembled to allow for the addition of small plastic agitator beads 14. Twenty 0.125 inch diameter plastic spheres are added into the elastomeric bladder 1. The device was reassembled and filled with fluid. Upon shaking, it was apparent that the beads were free to move about and did not interfere with the operation of the pump. The modified pump was now capable of mixing contained fluids with added efficiency.

EXAMPLE 4

A series of infusers were assembled in accordance with the general methods indicated in Example 1. The spherical infuser bladder internal diameter was much smaller than that used in Example 1. Agitators 14, were used, but with different diameter(s). In this series of experiments, anywhere from zero (control) to 286 balls were used to dissolve dextrose in water. In each case 0.5 grams of dextrose was used with 9 ml of water. The infusers were agitated in a similar manner to that of example 1. Measurements were made as to the retained volume associated with each design at the completion of the infusion of the fluid. The following table contains the test results:

| Infusion Device designation | Similar to Device in Figure | Number of Agitator Balls | Ball Diameter, Inches | Retained Volume, ml | Dissolution Time, Min:Sec |
|---|---|---|---|---|---|
| Control | | 0 | — | 3.6 | 3:28 |
| Inventive 4a | 1 | 1 | — | 0.0 | 2:01 |
| Inventive 4b | 3 | 29 | 3/16 | 2.0 | 1:11 |

-continued

| Infusion Device designation | Similar to Device in Figure | Number of Agitator Balls | Ball Diameter, Inches | Retained Volume, ml | Dissolution Time, Min:Sec |
|---|---|---|---|---|---|
| Inventive 4c | 4 | 18 | 3/16, 3/32 | 1.8 | 1:09 |
| Inventive 4d | 3 | 286 | 3/32 | 1.6 | 1:23 |

As can be seen in these examples, multiple agitator balls can significantly improve upon the dissolution times, at a cost of increased retained volume.

Although the Medicinal Liquid Infuser with Integral Agitator Means and the method of using the same according to the present invention has been described in the foregoing specification with considerable details, it is to be understood that modifications may be made to the invention which do not exceed the scope of the appended claims and modified forms of the present invention done by others skilled in the art to which the invention pertains will be considered infringements of this invention when those modified forms fall within the claimed scope of this invention.

We claim:

1. An infuser adapted to contain and, administer a fluid, and wherein said infuser comprises:
   a container,
   at least one bladder supported within said container,
   means for introducing liquid into said at least one bladder,
   means for withdrawing liquid from said at least one bladder,
   means within said at least one bladder for agitating liquid within said at least one bladder, and
   wherein said container has a mandrel secured to one end, said mandrel having means for communicating with said at least one bladder,
   wherein said mandrel has standoff means for preventing said means for agitating liquid from blocking said means for communicating with said at least one bladder,
   wherein said means within said at least one bladder for agitating liquid within said at least one bladder comprises at least one three dimensional object positioned within said bladder,
   wherein said three dimensional object is a pair of hemispheres, and
   wherein said hemispheres are secured together by a resilient element.

2. An infuser adapted to contain and, administer a fluid, and wherein said infuser comprises:
   a container,
   at least one bladder supported within said container,
   means for introducing liquid into said at least one bladder,
   means for withdrawing liquid from said at least one bladder,
   means within said at least one bladder for agitating liquid within said at least one bladder, and
   wherein said container has a mandrel secured to one end, said mandrel having means for communicating with said at least one bladder,
   wherein said mandrel has standoff means for preventing said means for agitating liquid from blocking said means for communicating with said at least one bladder,
   wherein said means within said at least one bladder for agitating liquid within said at least one bladder comprises at least one three dimensional object positioned within said bladder, wherein said means for agitating liquid is a pair of hemispheres, and wherein said hemispheres are secured together by a resilient element.

3. An infuser adapted to contain and administer a fluid, and wherein said infuser comprises:

a container, at least one bladder supported within said container, means for introducing liquid into said at least one bladder, means for withdrawing liquid from said at least one bladder, means within said at least one bladder for agitating liquid within said at least one bladder, and wherein said means within said at least one bladder for agitating liquid within said at least one bladder comprises at least one three dimensional object positioned within said bladder, and wherein said three dimensional object is a pair of hemispheres, and wherein said hemispheres are secured together by a resilient element.

4. An infuser adapted to contain and administer a fluid, and wherein said infuser comprises:

a container, at least one bladder supported within said container, means for introducing liquid into said at least one bladder, means for withdrawing liquid from said at least one bladder, means within said at least one bladder for agitating liquid within said at least one bladder, and wherein said container has a mandrel secured to one end, said mandrel having means for communicating with said at least one bladder, and wherein said means for communicating with said at least one bladder comprises a cylinder having a fluid path, an outlet from said fluid path is positioned on an end of said cylinder, and wherein said end of said cylinder has standoff means for preventing said means for agitating liquid from blocking said outlet from said fluid path, said standoff means extending away from said end of said cylinder.

5. The infuser as claimed in claim 4, wherein said standoff means is a plurality of raised areas.

6. The infuser as claimed in claim 4, wherein there are a plurality of bladders, and each bladder fits within another bladder.

7. The infuser as claimed in claim 4, wherein said means for agitating liquid is a plurality of spheres, and said plurality of spheres are of different sizes.

* * * * *